United States Patent
Koehler et al.

(10) Patent No.: US 8,615,289 B2
(45) Date of Patent: Dec. 24, 2013

(54) DRUG APPLICATION DURING A CT SCAN

(75) Inventors: Thomas Koehler, Norderstedt (DE); Michael Grass, Buchholz in der Nordheide (DE)

(73) Assignee: Koninklijke Philips N.V., Eindhoven (NL)

( * ) Notice: Subject to any disclaimer, the term of this patent is extended or adjusted under 35 U.S.C. 154(b) by 1864 days.

(21) Appl. No.: 10/598,004

(22) PCT Filed: Feb. 15, 2005

(86) PCT No.: PCT/IB2005/050576
§ 371 (c)(1),
(2), (4) Date: May 10, 2007

(87) PCT Pub. No.: WO2005/082253
PCT Pub. Date: Sep. 9, 2005

(65) Prior Publication Data
US 2008/0027307 A1    Jan. 31, 2008

(30) Foreign Application Priority Data
Feb. 20, 2004   (EP) .................................... 04100688

(51) Int. Cl.
*A61B 5/055*   (2006.01)
*A61B 8/00*   (2006.01)
*A61H 1/00*   (2006.01)

(52) U.S. Cl.
USPC ................ 600/427; 600/431; 600/439; 601/2

(58) Field of Classification Search
None
See application file for complete search history.

(56) References Cited

U.S. PATENT DOCUMENTS

| | | | |
|---|---|---|---|
| 5,042,497 A | 8/1991 | Shapland | |
| 5,190,766 A * | 3/1993 | Ishihara | 424/489 |
| 5,542,935 A * | 8/1996 | Unger et al. | 604/190 |
| 5,580,575 A | 12/1996 | Unger et al. | |
| 6,397,098 B1 * | 5/2002 | Uber et al. | 600/431 |
| 6,475,148 B1 | 11/2002 | Jackson et al. | |
| 6,571,122 B2 | 5/2003 | Schroeppel et al. | |
| 6,628,981 B2 | 9/2003 | Baker et al. | |
| 7,358,226 B2 * | 4/2008 | Dayton et al. | 514/2 |
| 2002/0151792 A1 | 10/2002 | Conston et al. | |
| 2003/0092983 A1 | 5/2003 | Baker et al. | |

OTHER PUBLICATIONS

Barrett, J.; Impact Special Interest Report: Cardiac CT Scanning; MHRA Evaluation Report No. 03076; 2003.
Blomley, M.J., et al.; Science, medicine, and the future: Microbubble contrast agents: a new era in ultrasound; 2001; Clinical Review:BMJ. British Medical Journal; 322(7296)1222-1225.
Giesler, T., et al.; Noninvasive visualization of coronary arteries using contrast-enhanced multidetector CT: influence of heart rate on image quality and stenosis detection; 2002; AJR; 179:911-916.
Kestin, I.; Control of Heart Rate; 1993; Physiology; 3;http://www.nda.ox.ac.uk/wfsa/html/u03_011.htm.

* cited by examiner

*Primary Examiner* — Long V. Le
*Assistant Examiner* — Angela M Hoffa

(57) ABSTRACT

Controlled local application of drugs to a certain part of a body of a patient may be of major importance during a cardiac CT scan. By transporting the drugs in containers which prevent an application of the drugs and by rupturing only those containers which are located in the vicinity of the part of the body of a patient to which the drugs have to be applied, a local application of the drugs may be performed. According to an exemplary embodiment of the present invention, the rupturing and therefore the application of the drugs may be triggered by a monitoring algorithm which evaluates changes in the heart beat rate of the patient. Advantageously, the method allows for a local delivery of the drugs on a fine time scale and therefore for a fast control of the heart beat rate during the CT scan.

17 Claims, 4 Drawing Sheets

DRUG APPLICATION DURING A CT SCAN

BACKGROUND OF THE INVENTION

The present invention relates to the field of drug application during a CT scan. In particular, the present invention relates to a method of controlling a local application of drugs to a part of the body of a patient during a CT scan, a CT scanner system adapted for controlling a local application of drugs, to a computer program for controlling the local application of drugs and to a use of containers for controlling a local application of a drug to a part of the body of a patient during a CT scan.

Local application of drugs to a part of the body of a patient is well known in the field of medical practice. For example, in the case of dental surgery, the dentist may apply an anesthetic locally to that part of the mouth of the patient where the surgery is to be carried out. The local application is thereby performed by injecting the anesthetic manually into the tissue of the patient.

In the field of cardiac CT imaging, the temporal resolution of the cardiac CT images depends sensitively on the ratio between heart beat rate and the gantry rotation frequency. During a typical cardiac CT scan, the heart beat rate may drop at the beginning as a reaction of the heart to the inflow of contrast agent. In the second half of the scan however, the heart beat rate may increase again as a result of the reduced oxygen content in the blood since the patient holds his breath. The heart beat rate may also be influenced by factors like stress, fear, emotion caused by the noise of the apparatus and so on. The varying heart beat rate leads to a spatially varying temporal resolution and prohibits the use of a patient-specific gantry rotation time in order to optimize the temporal resolution. Therefore, in order to avoid motion artifacts or a spatially varying temporal resolution, the heart beat rate has to be kept constant during the cardiac CT scan.

BRIEF DESCRIPTION OF THE INVENTION

It is an object of the present invention to provide for an improved CT imaging.

According to an exemplary embodiment of the present invention, the above object may be solved by a method of controlling a local application of drugs to a part of the body of a patient during a CT scan, wherein the drugs are transported in containers suitable for introduction into a bloodstream of the patient. The containers prevent an application of the drugs, wherein a first drug is transported in a first container. By rupturing the first container in proximity to the part of the body, a local application of the first drug to the part of the body is achieved.

Advantageously, this exemplary embodiment of the present invention allows for a delivery of the drugs by the bloodstream to the part of the body to which the drugs have to be applied before the containers are ruptured and therefore release the drug.

According to another exemplary embodiment of the present invention, a heart beat rate of the heart of a patient is monitored, wherein the part of the body the drugs are locally applied to is the heart of the patient. The first drug is locally applied to the heart of the patient by rupturing the first container or micro-bubble in proximity to the heart and the rupturing of the first container is performed on the basis of the heart beat rate, resulting in a controlled change of the heart beat rate.

Advantageously, according to this exemplary embodiment of the present invention, the heart beat rate of the patient is monitored during the cardiac CT scan and, if a change in the heart beat rate is detected, for example a decrease of the heart beat rate, the first container, which is located in proximity to the heart of the patient, is ruptured and therefore the first drug is released and applied to the heart of the patient. The application of the first drug results in a change of the heart beat rate, for example an increase of the heart beat rate.

According to another exemplary embodiment of the present invention, the first container has a first resonance frequency, such that when an ultrasonic energy pulse with a first frequency corresponding to the first resonance frequency is applied to the first container, a rupture of the first container occurs and the first drug is released from the first container. The rupturing is hereby performed by means of a destruction device, wherein the destruction device generates focused ultrasound pulses, which have a first frequency corresponding to the first resonance frequency of the first container.

Advantageously, focusing the ultrasound pulses for the rupturing or destruction of the first container allows for a localized release of the first drug, for example, in proximity to the heart of the patient. Furthermore, according to this exemplary embodiment of the present invention, the first container may only rupture, if not only an ultrasonic energy pulse is applied to the first container, but also the applied ultrasonic energy pulse has a certain first frequency, which corresponds to a resonance frequency of the first container.

According to another exemplary embodiment of the present invention, the first container has a first resonance frequency, such that when an electro-magnetic energy beam with a first frequency corresponding to the first resonance frequency is applied to the first container, a rupture of the first container occurs and the first drug is released from the first container, wherein the rupturing of the first container is performed by means of a destruction device. The destruction device generates a beam of electromagnetic radiation and the electromagnetic radiation has a first frequency corresponding to the first resonance frequency of the first container.

Advantageously, this may allow for a local destruction or rupturing of the first container by a very well focused and easily tunable electromagnetic radiation beam of a first frequency.

According to another exemplary embodiment of the present invention, a second drug is transported in a second container, wherein the first container has a first resonance frequency and the second container has a second resonance frequency. The first resonance frequency is different from the second resonance frequency.

Therefore, according to this exemplary embodiment of the present invention, a local application of a first drug or a second drug may be provided, wherein the first drug is applied by rupturing the first container and the second drug is applied by rupturing the second container. Since the resonance frequency of the first container is different from the resonance frequency of the second container, a selective destruction or a rupturing of the first and second containers may be performed.

According to another exemplary embodiment of the present invention, the application of the first drug increases the heart beat rate and the application of the second drug decreases the heart beat rate. Therefore, by selectively destroying either the first container or the second container in the vicinity of the heart, the heart beat rate may effectively be controlled.

According to another exemplary embodiment of the present invention, the containers are micro-bubbles. The micro-bubbles may have a structure and materials such as, for example, disclosed in the US 2002/0151792 A1, which is hereby incorporated by reference. The micro-bubbles may contain a contrast agent, which is visible in images registered by means of a nuclear medical imaging system. The micro-bubbles may be suitable for introduction into a blood stream of a subject, such as a patient, animal or mammal.

According to another exemplary embodiment of the present invention, a CT scanner system is provided, which is adapted for controlling a local application of drugs to a part of the body of a patient during a CT scan, comprising a CT scanner, a monitoring device, a data processing device and a destruction device. The drugs are transported in containers suitable for introduction into a bloodstream of the patient and preventing an application of the drugs, wherein a first drug is transported in a first container. The CT scanner is adapted for acquisition of an image of the part of the body and the monitoring device is adapted for monitoring a heart beat rate of the heart of a patient during the CT scan. Furthermore, the destruction device is adapted for rupturing the first container in proximity to the part of the body, resulting in a local application of the first drug to the part of the body and the data processing device is adapted for triggering the rupturing of the first container on the basis of the heart beat rate.

Advantageously, this may allow for a controlled local application of drugs during a CT scan.

According to another exemplary embodiment of the present invention, the first drug is locally applied to the heart of the patient on the basis of the heart beat rate, wherein the first container has a resonance frequency. The destruction device is adapted for generating either focused ultrasound pulses or a beam of electromagnetic radiation. Furthermore, the frequency of the one of focused ultrasound pulses and the beam of electromagnetic radiation corresponds to the resonance frequency of the first container.

Advantageously, this may allow for a selective destruction or rupturing of the first container by setting the frequency of either the focused ultrasound pulses or the beam of electromagnetic radiation to the resonance frequency of the first container.

The present invention also relates to a computer program, which may, for example, be executed on a processor. Such computer programs may be part of for example, a CT scanner system. These computer programs may be preferably loaded into working memories of data processors. The data processors are thus equipped to carry out exemplary embodiments of the methods of the present invention. The computer programs may be stored on a computer readable medium, such as a CD-ROM. The computer programs may also be presented over a network such as the WorldWideWeb, and may be downloaded into the working memory of a data processor from such networks.

Another exemplary embodiment of the present invention relates to the use of containers for controlling a local application of a drug to a part of the body of a patient during a CT scan.

It may be seen as the gist of an exemplary embodiment of the present invention that only containers comprising a certain drug and which are located in the vicinity of the part of the body of a patient to which a certain drug has to be applied are ruptured or destroyed. According to an exemplary embodiment of the present invention, the rupturing of the containers and therefore the application of the drug is performed at a time determined by a monitoring algorithm on the basis of the heart beat rate of the patient, providing for a fast change of the heart beat rate. Advantageously, this may allow to reduce variations in the heart beat rate of a patient during a cardiac CT scan and therefore may result in an improved image quality of an image of the heart.

These and other aspects of the present invention will become apparent from and elucidated with reference to the embodiments described hereinafter.

BRIEF DESCRIPTION OF THE DRAWINGS

Exemplary embodiments of the present invention will be described in the following, with reference to the following drawings.

DETAILED DESCIRTION OF THE INVENTION

Figure 1:
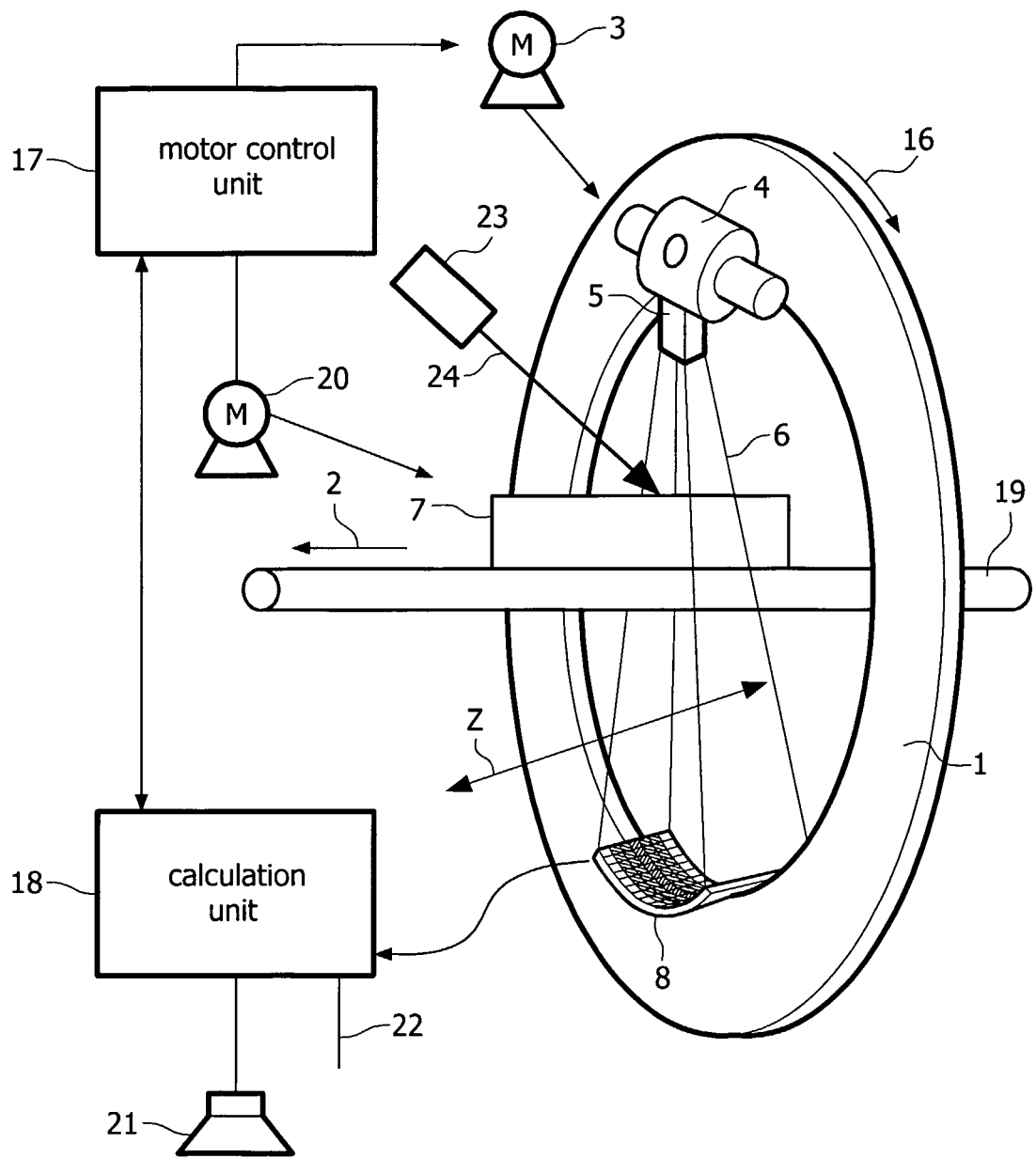
FIG. 1 shows a simplified schematic representation of an embodiment of a computed tomography (CT) scanner system comprising a destruction device according to the present invention.

FIG. 1 shows a simplified schematic representation of an exemplary embodiment of a CT (computed tomography) scanner system according to the present invention. With reference to this exemplary embodiment, the present invention will be described for the application in medical imaging. However, it should be noted that the present invention is not limited to the application in the field of medical imaging, but may be used in applications such as baggage inspection to detect hazardous materials, such as explosives, in items of baggage or other industrial applications, such as material testing.

The scanner depicted in FIG. 1 is a cone beam CT scanner. The CT scanner depicted in FIG. 1 comprises a gantry 1, which is rotatable around a rotational axis 2. The gantry is driven by means of a motor 3. Reference numeral 4 designates a source of radiation such as an x-ray source, which, according to an aspect of the present invention, emits a polychromatic radiation.

Reference numeral 5 designates an aperture system which forms the radiation beam emitted from the radiation source to a cone shaped radiation beam 6.

The cone beam 6 is directed such that it penetrates an object of interest 7 arranged in the center of the gantry 1, i.e. in an examination region of the CT scanner and impinges onto the detector 8. As may be taken from FIG. 1, the detector 8 is arranged on the gantry 1 opposite the source of radiation 4, such that the surface of the detector 8 is covered by the cone beam 6. The detector 8 depicted in FIG. 1 comprises a plurality of detector elements.

During a scan of the object of interest 7, the source of radiation 4, the aperture system 5 and detector 8 are rotated along gantry 1 in the direction indicated by arrow 16. For rotation of the gantry 1 with the source of radiation 4, the aperture system 5 and the detector 8, the motor 3 is connected to a motor control unit 17, which is connected to a calculation unit 18.

In FIG. 1, the object of interest is disposed on a conveyor belt 19. During the scan of the object of interest 7, while the gantry 1 rotates around the patient 7, the conveyor belt 19 displaces the object of interest 7 along a direction parallel to the rotational axis 2 of the gantry 1. By this, the object of interest 7 is scanned along a helical scan path. The conveyor belt 19 may also be stopped during the scans to thereby measure single slices. Instead of providing a conveyor belt 19, for example, in medical applications, where the object of interest 7 is a patient, a movable table is used. However, it should be noted that in all of the described cases it is also possible to perform a circular scan, where there is no displacement in a direction parallel to the rotational axis 2, but only the rotation of the gantry 1 around the rotational axis 2.

The detector 8 is connected to the calculation unit 18. The calculation unit 18 receives the detection result, i.e. the read-outs from the detector element of the detector 8, and determines a scanning result on the basis of the read-outs. The detector elements of the detector 8 may be adapted to measure the attenuation caused to the cone beam 6 by the object of interest. Furthermore, the calculation unit 18 communicates with the motor control unit 17 in order to coordinate the movement of the gantry 1 with motor 3 and 20 or with the conveyor belt 19.

The calculation unit 18 may be adapted for reconstructing an image from read-outs of the detector 8. The image generated by the calculation unit 18 may be output to a display (not shown in FIG. 1) via an interface 22.

The calculation unit which may be realized by a data processing device may also be adapted to perform a triggering of the rupturing or destruction of the first container on the basis of a heart beat rate of the heart of a patient. According to an aspect of the present invention, the heart beat rate of the heart of the patient is monitored and evaluated. Based on the evaluation of the heart beat rate, the data processing device may trigger a destruction device 23 to emit a focused ultrasound pulse 24. The ultrasound pulse 24 is focused on the neighborhood of the heart of the patient or on the heart itself and has a frequency which corresponds to a resonance frequency of containers or micro-bubbles containing a drug. According to an aspect of the present invention, these micro-bubbles are visible to an ultrasound imaging system and may furthermore be visible in a nuclear medical imaging system such as, for example, PET or SPECT. For this, the micro-bubbles may comprise a radio pharmaceutical such as, e.g. 18F, 11C, 13N or 15O for PET in combination with, for example, 18F-FDG (fluor deoxy glucose), 11C-acetate and 11C-methionine, 13N—NH3 and H2 15O, or Tc-99m for SPECT. The micro-bubbles are designed such that they are suitable for introduction into a bloodstream of a subject, for example a patient. The micro-bubbles may have diameters within the range of about 1 to 10 μm. Details with respect to the material of the micro-bubbles and the construction of the micro-bubbles may, for example, be taken from US 2002/0151792 A1, which is hereby incorporated by reference.

Furthermore, as may be taken from FIG. 1, the calculation unit 18 may be connected to a loudspeaker 21 to, for example, automatically output an alarm.

Figure 2:
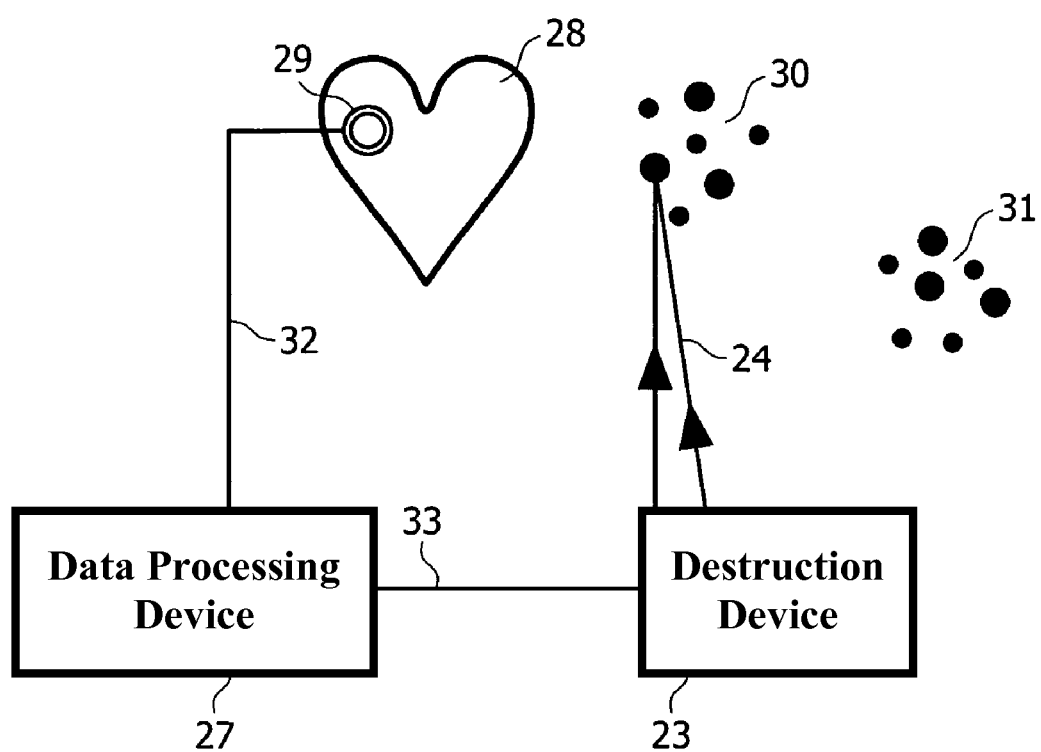
FIG. 2 shows a schematic representation of a feedback loop according to an exemplary embodiment of the present invention.

FIG. 2 shows a schematic representation of a feedback loop according to an exemplary embodiment of the present invention. The feedback loop may be implemented in a CT scanner system, as depicted in FIG. 1. A monitoring device 29 monitors or measures the heart beat rate of the heart 28 of a patient during a cardiac CT scan. Information about the monitored heart beat rate is transmitted from monitoring device 29 to a data processing device 27 via line 32. The data processing device 27 is adapted for triggering the rupturing or destruction of containers 30 on the basis of the heart beat rate. In case the data processing device 27 comes to the conclusion that, after evaluation of the heart beat rate, a change of the heart beat rate has to be initiated, it sends a triggering signal to the destruction device 23 via line 33. The destruction device 23 is adapted for rupturing the containers 30, which are located in proximity to the heart of the patient by emission of focused ultrasound pulses 24, resulting in a local application of the drug contained in the micro-bubbles 30 to the heart of the patient.

Destruction device 23 generates a focused beam of ultrasound pulses 24, which is aimed at the heart 28 of the patient or at the neighborhood of the heart, where the containers or micro-bubbles 30 are located. Therefore, only the containers 30 in the vicinity of the heart 28 are destroyed. No containers 31, which are located at a distance away from the heart 28, are destroyed or ruptured. Therefore, the drugs are only released close to the heart 28.

The micro-bubbles 30 may comprise a cavity (not shown in FIG. 2). The wall of the micro-bubbles or containers 30 have a controlled fragility, such that a rupture can be created in the wall by means of a pre-determined ultrasound energy. The cavity of the micro-bubbles 30 contains a drug such as adrenalin for increasing the heart beat rate or acetic choline for decreasing the heart beat rate. Both drugs, adrenalin and acetic choline, are part of a normal human control loop for the heart beat rate. Adrenalin acts on the entire heart muscle, while acetic choline acts on the sinus node only. Thus, both drugs act locally and directly on the heart. Both drugs do not pass the cell membranes and act by modifying the permeability of the cell membranes for certain ions. This way of acting is known to be very fast and consequently these two drugs can be used to control the heart beat rate during a CT scan.

In order to ensure the visibility of the micro-bubble in ultrasound imaging, the cavity may contain air or other suitable gas allowing for sufficient compressibility and oscillation capability of the micro-bubble in case it is subjected to ultrasound. However, it is also possible to include the air or gas in the wall of the micro-bubble. The wall may be made of a lipid material.

According to a variant of the above exemplary embodiment, the micro-bubble may be a gas-filled microsphere or comprise liposomes containing the drug for local application. The drug may be located in cavities of the microsphere or liposomes, in the walls or may be attached to an outside of the walls of the microsphere or liposomes. According to an aspect of the present invention, the drug may be arranged in the microsphere or liposomes in the same manner as the therapeutic compounds of the therapeutic drug delivery system disclosed in the U.S. Pat. No. 5,580,575, which is hereby incorporated by reference. Also, the composition of the walls of the microsphere or liposomes according to this exemplary embodiment of the present invention may be the same as of the microsphere or liposomes comprising the therapeutic compounds of the therapeutic drug delivery system disclosed in the U.S. Pat. No. 5,580,575, which is hereby incorporated by reference. The gas-filled microspheres or liposomes are visible in ultrasound imaging.

According to an exemplary embodiment of the present invention, the two drugs are transported in different containers. Adrenalin, which increases the heart beat rate, is transported in a first container type and acetic choline, which decreases the heart beat rate, is transported in a second container type. The first container has a first resonance frequency and the second container has a second resonance frequency, wherein the first resonance frequency is different from the second resonance frequency. This may, for example, be achieved by different sizes of the first containers and the second containers or, for example, by different wall thicknesses of the first containers and the second containers. However, since the first containers and the second containers have different resonance frequencies, they may be addressed individually by the destruction device 23. Therefore, it may be possible to destroy or rupture the first container type by means of a focused ultrasound pulse 24 with a first frequency and at the same time not to destroy or rupture the second container type, which may be located in the vicinity of the first container type. On the other hand, by changing the frequency of the focused ultrasound pulse 24, it may be possible to address and therefore to destroy or rupture the second container type in the vicinity of the heart 28 without effecting the first container type.

Furthermore, by focusing the ultrasound pulse 24 and aiming the focused ultrasound pulse 24 at an area located close to the heart 28 or even inside the heart 28, containers 31 are not influenced by the ultrasound pulses 24 and are therefore not destroyed.

It should be understood that containers 30 and 31 may comprise two different types of containers, namely first containers with a first resonance frequency and second containers with a second resonance frequency. The first containers comprise a first type of drug and the second containers comprise a second type of drug.

It should also be noted that the assembly depicted in FIG. 2 is designed in the form of a feedback loop. By monitoring the heart beat rate and evaluating the monitored heart beat rate, changes in the heart beat rate may be identified and a corresponding beam 24 may be emitted in order to destroy a certain container type in the vicinity of the heart, resulting in either an increase or a decrease of the heart beat rate. Of course, the overall effect may be that no major changes in the heart beat rate occur, since a measured increase of the heart beat rate will result in a destruction of a second container leading to a release of acetic choline and therefore to a reduction of the heart beat rate and vice versa.

Instead of being contained in the cavity of the micro-bubble, the drugs may also be comprised in the wall of the micro-bubble.

Furthermore, it should be noted that the beam 24 may be an electro-magnetic energy beam with a frequency corresponding to the resonance frequency of the first container or the second container 30. The resonance frequency may be a frequency of a vibration mode or a deformation oscillation of the container or micro-bubble, or the resonance frequency may correspond to a transformation energy or energy difference between two energy states of a molecule of the container. By applying the electromagnetic radiation to the container, the whole container or certain molecules of the container may absorb energy in such a way that the container ruptures, resulting in an outflow of the drugs contained inside the container.

Figure 3:
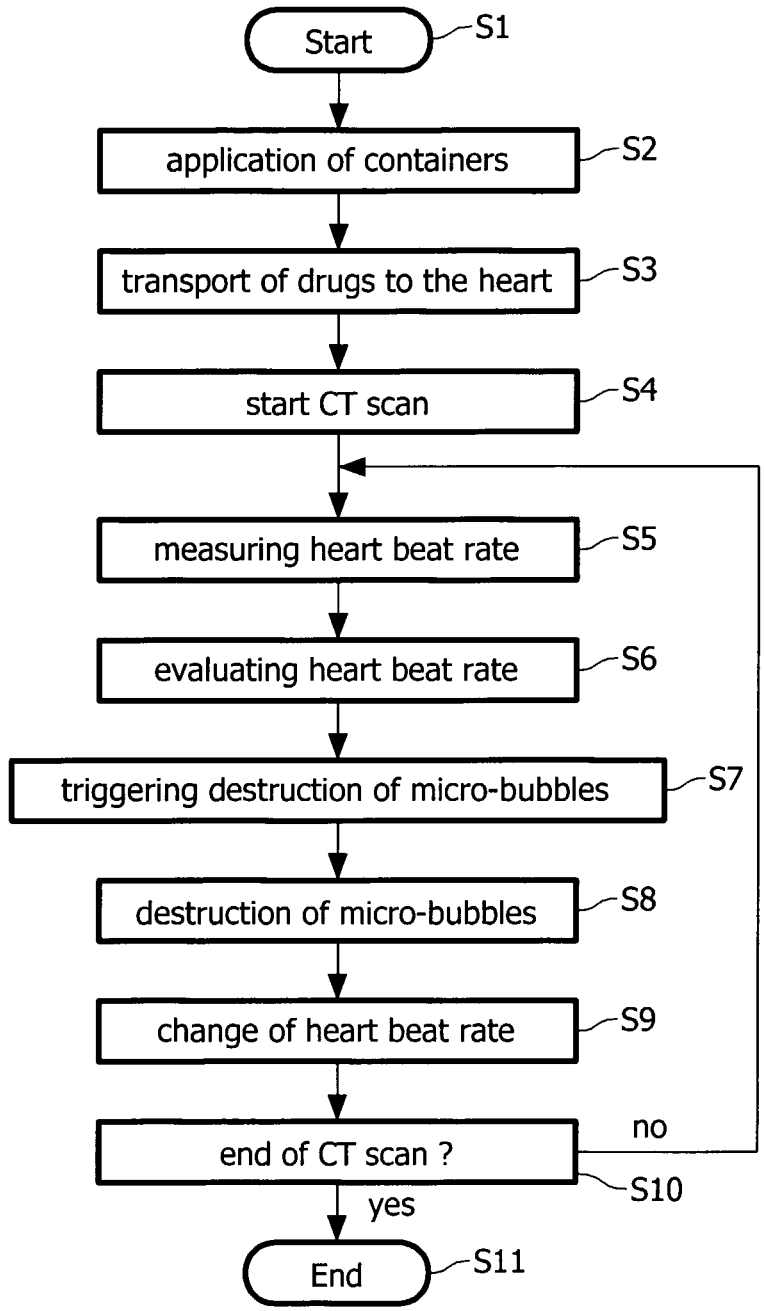
FIG. 3 shows a flow-chart of an exemplary embodiment of a method according to the present invention.

In the following, a method according to an exemplary embodiment of the present invention and the use of containers for controlling a local application of a drug to a part of the body of a patient during a CT scan will be described with reference to FIG. 3.

After the start in step S1, the first and second containers are applied to the bloodstream of a patient in step S2, e.g. by an injection. Then, in step S3, by means of the bloodstream of the patient, the containers are transported to the region of interest of the patient to be examined, e.g. the heart of the patient. After that, in step S4, the CT scan starts, for example, by acquisition of projection data of the heart of the patient.

In step S5, a measurement of the actual heart beat rate is performed, e.g. by an ECG, and in step S6 the measured heart beat rate is evaluated. By then, the injected containers have been transported to the heart of the patient by means of the bloodstream. If the data processing device which evaluates the heart beat rate observes a change in the heart beat rate, it may trigger a destruction of micro-bubbles S7 in the vicinity of the heart. The micro-bubbles may then be destroyed by means of a focused ultrasound pulse at the resonance frequency of the micro-bubbles, leading to a local delivery of the drugs. The micro-bubbles used for the transportation of the drugs must have different sizes and thus different resonance frequencies in order to allow a delivery of only one of the two drugs at a time. For example, if the data processing device observes an increase of the heart beat rate, it triggers a destruction of the second type of micro-bubbles, namely the micro-bubbles containing acetic choline, which decreases the heart beat rate.

After destruction of the micro-bubbles in step S8 by the destruction device, the drugs are applied locally to the heart of the patient, resulting in a change of the heart beat rate in step S9. Then, in step S10, the data processing device decides whether the CT scan continues or whether it is finished. If the CT scan continues, the method jumps back to step S5 and the heart beat rate is again measured. This process may be understood as a feedback loop in which a measured change of the heart beat rate which is not desired results in a local application of a drug which changes the heart beat rate in the other direction.

If, however, in step S10, the data processing device determines that the end of the CT scan has been reached, no further measuring of the heart beat rate is performed and the process of projection data acquisition and control of the heart beat rate ends with step S11.

Figure 4:
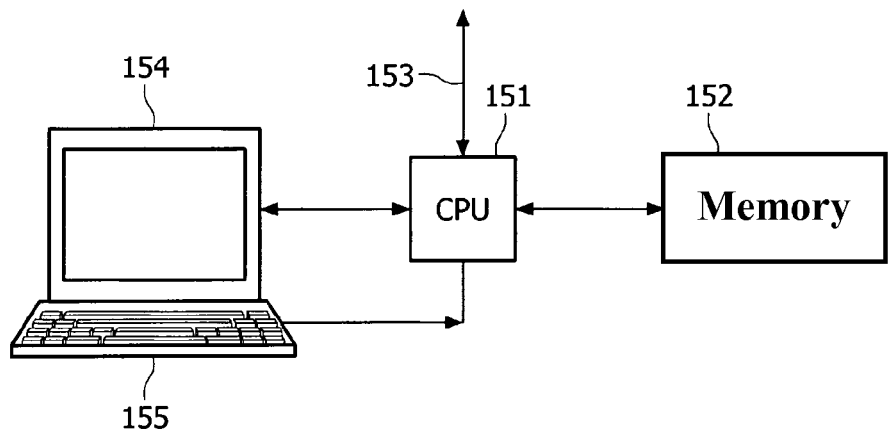
FIG. 4 shows an exemplary embodiment of a data processing device according to the present invention for executing an exemplary embodiment of a method in accordance with the present invention.

FIG. 4 depicts an exemplary embodiment of a data processing device according to the present invention for executing an exemplary embodiment of a method in accordance with the present invention. The data processing device depicted in FIG. 4 comprises a central processing unit (CPU) or image processor 151 connected to a memory 152 for storing an image depicting an object of interest, such as a patient. The data processor 151 may be connected to a plurality of input/output network or diagnosis devices, such as an MR device or a CT device. The data processor may furthermore be connected to a display device 154, for example, a computer monitor, for displaying information or an image computed or adapted in the data processor 151. An operator or user may interact with the data processor 151 via a keyboard 155 and/or other output devices, which are not depicted in FIG. 4.

Furthermore, via the bus system 153, it is also possible to connect the image processing and control processor 151 to, for example, a motion monitor, which monitors a motion of the object of interest. In case, for example, a lung of a patient is imaged, the motion sensor may be an exhalation sensor. In case the heart is imaged, the motion sensor may be an electrocardiogram (ECG).

Figure 5:
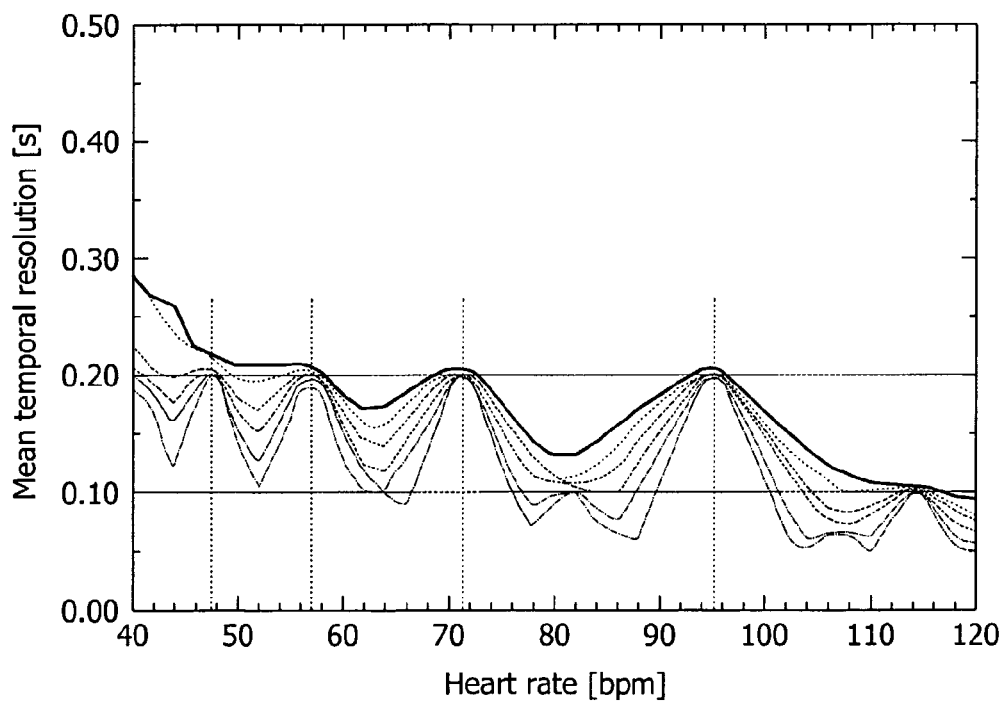
FIG. 5 shows the mean temporal resolution versus heart rate at a rotation time of 0.42 seconds.

FIG. 5 shows a simulation of the mean temporal resolution versus the heart rate of a patient at a rotation time of the radiation source $t_{rot}$=0.42 sec. at a constant heart rate. The x-axis shows the heart rate, beginning at 40 beats per minute on the left side up to 120 beats per minute on the right side. The y-axis shows the mean temporal resolution from 0.00 to 0.50 sec. The six different curves represent the mean temporal resolution versus the heart rate at six different relative pitches. The uppermost curve represents a pitch of 0.30, the dotted curve below represents the mean temporal resolution at a relative pitch of 0.27, the curve below this represents the mean temporal resolution at a relative pitch of 0.24, the curve below represents the mean temporal resolution at a relative pitch of 0.21, the second lowest curve represents the mean temporal resolution at a relative pitch of 0.18 and the lowest curve represents the mean temporal resolution versus heart rate at a relative pitch of 0.15. The gating of each curve is positioned at 85% RR and the rotation time is 0.42 sec. Before the scan, the relative pitch is selected, e.g. 0.15 (lowest curve). As can be seen from the lowest curve, at 88 beats per minute the mean temporal resolution is about 70 milli-seconds. If the heart beat rate of the patient increases to 95 bpm, the temporal resolution decreases to about 200 milli-seconds. Therefore, an increase in the heart beat rate of about 10% results in a reduction of the mean temporal resolution by a factor 2 to 3. Therefore, in order to obtain an acceptable mean temporal resolution, it may be advantageous to keep the heart beat rate constant during data acquisition. According to an exemplary embodiment of the present invention, this may be achieved by rupturing certain containers comprising respective drugs at a time determined by a monitoring algorithm on the basis of the heart beat rate (which may be monitored by an electro-cardiogram) of the patient. By doing so, a fast change of the heart beat rate may be triggered, allowing for a reduction in variations of the heart beat rate of the patient during a cardiac CT scan and therefore resulting in an improved image quality of an image of the heart.

We claim:

1. A method of controlling a local application of drugs to a part of a body of a patient during a CT scan, wherein the drugs are transported in containers suitable for introduction into a bloodstream of the patient; wherein the containers prevent an application of the drugs; wherein a first drug is transported in a first container, wherein a second drug is transported in a second container; wherein the first container has a first resonance frequency; wherein the second container has a second resonance frequency; and wherein the first resonance frequency is different from the second resonance frequency; the method comprising the steps of: applying the first container and the second container to the bloodstream of the patient; monitoring a heart beat rate of the patient during the CT scan; and selectively rupturing at least one of the first container and the second container in proximity to the part of the body on the basis of the monitored heart beat rate, resulting in a local application of at least one of the first drug and the second drug respectively to the part of the body and a controlled change of the heart beat rate of the patient to reduce variations in the heart beat rate during the CT scan.

2. The method according to claim 1, wherein the part of the body the drugs are locally applied to is the heart of the patient; and wherein the first drug is locally applied to the heart of the patient by rupturing the first container in proximity to the heart.

3. The method according to claim 1, wherein when an ultrasonic energy pulse with a first frequency corresponding to the first resonance frequency is applied to the first container, a rupture of the first container occurs and the first drug is released from the first container; wherein the rupturing of the first container is performed by a destruction device; wherein the destruction device generates focused ultrasound pulses; and wherein the ultrasound pulses have a first frequency corresponding to the first resonance frequency of the first container.

4. The method according to claim 1, wherein when an electromagnetic energy beam with a first frequency corresponding to the first resonance frequency is applied to the first container, a rupture of the first container occurs and the first drug is released from the first container; wherein the rupturing of the first container is performed by a destruction device; wherein the destruction device generates a beam of electromagnetic radiation; and wherein the electromagnetic radiation has a first frequency corresponding to the first resonance frequency of the first container.

5. The method according to claim 1, wherein the application of the first drug increases the heart beat rate; and wherein the application of the second drug decreases the heart beat rate.

6. The method according to claim 1, wherein the containers are micro-bubbles.

7. The CT scanner system according to claim 1, wherein the containers are micro-bubbles.

8. A CT scanner system adapted for controlling a local application of drugs to a part of a body of a patient during a CT scan, comprising:
a CT scanner; a monitoring device; a data processing device; and a destruction device; wherein a first drug is transported in a first container; wherein a second drug is transported in a second container; wherein the second drug is different from the first drug; the first container has a first resonance frequency; the second container has a second resonance frequency; and wherein the first resonance frequency is different from the second resonance frequency; wherein the drugs are transported in containers suitable for introduction into a bloodstream of the patient and preventing an application of the drugs; wherein the CT scanner is adapted for acquisition of an image of the part of the body; wherein the monitoring device is adapted for monitoring a heart beat rate of a heart of the patient during the CT scan; wherein the destruction device is configured to selectively rupture at least one of the first container and the second container in proximity to the part of the body, resulting in a local application of at least one of the first drug and the second drug respectively to the part of the body and a controlled change of the heart beat rate of the patient to reduce variations in the heart beat rate during the CT scan;
and wherein the data processing device is configured to selectively trigger the rupturing of at least one of the first container and the second container on the basis of the monitored heart beat rate.

9. The CT scanner system according to claim 8, wherein the first drug is locally applied to the heart of the patient on the basis of the heart beat rate; wherein the destruction device is adapted for generating one of focused ultrasound pulses and a beam of electromagnetic radiation; and wherein a frequency of the one of focused ultrasound pulses and the beam of electromagnetic radiation corresponds to the first resonance frequency of the first container.

10. The CT scanner system according to claim 8, wherein the part of the body the at least one drug is locally applied to is the heart of the patient.

11. The CT scanner system according to claim 8, wherein when an ultrasonic energy pulse with a first frequency corresponding to the first resonance frequency is applied to the first container, a rupture of the first container occurs and the first drug is released from the first container; wherein the rupturing of the first container is performed by a destruction device; wherein the destruction device generates focused ultrasound pulses; and wherein the ultrasound pulses have a first frequency corresponding to the first resonance frequency of the first container.

12. The CT scanner system according to claim 8, wherein when an electromagnetic energy beam with a first frequency corresponding to the first resonance frequency is applied to the first container, a rupture of the first container occurs and the first drug is released from the first container; wherein the rupturing of the first container is performed by a destruction device; wherein the destruction device generates a beam of electromagnetic radiation; and wherein the electromagnetic radiation has a first frequency corresponding to the first resonance frequency of the first container.

13. The CT scanner system according to claim 8, wherein application of the first drug increases the heart beat rate, and application of the second drug decreases the heart beat rate.

14. A non-transitory computer program for controlling a local application of drugs to a part of a body of a patient during a CT scan, wherein the computer program causes a processor to perform the following operation when the computer program is executed on the processor: evaluating a heart beat rate of a heart of the patient during the CT scan; selectively triggering a rupturing of at least one of a first container and a second container comprising a first drug and a second drug respectively on the basis of the evaluation of the heart beat rate; wherein the first drug is transported in the first container; wherein the second drug is transported in the second container; wherein the second drug is different from the first drug; the first container has a first resonance frequency for rupturing the first container; the second container has a second resonance frequency for rupturing the second container; and wherein the first resonance frequency is different from the second resonance frequency; wherein the first container is located in proximity to the part of the body, resulting in a local application of the first drug to the part of the body and a controlled change of the heart beat rate of the patient to reduce variations in the heart beat rate during the CT scan.

15. An imaging scanner system comprising:
  a scanner adapted for acquiring an image of the heart in an imaging scan;
  a monitoring device adapted to monitor a heart beat rate of the patient during the imaging scan;
  a destruction device configured to selectively rupture at least one of a first container and a second container in proximity to the heart, resulting in a local application of at least one of a first drug and a second drug stored in the first container and the second container respectively and a controlled change of the patient's heart beat rate to reduce variations in the heart beat rate during the imaging scan; wherein the first drug is transported in the first container; wherein the second drug is transported in the second container; wherein the second drug is different from the first drug; the first container has a first resonance frequency; the second container has a second resonance frequency; and wherein the first resonance frequency is different from the second resonance frequency; and
  a data processing device configured to selectively trigger the destruction device, based on data received from the monitoring device.

16. The imaging scanner of claim 15 wherein the destruction device generates one of an ultrasound pulse and an electromagnetic radiation pulse in order to rupture the first container.

17. The imaging scanner of claim 16 wherein the destruction device is adapted to generate pulses having different frequencies in order to rupture containers having different resonance frequencies.

* * * * *